United States Patent
Floros et al.

(10) Patent No.: US 7,041,638 B2
(45) Date of Patent: May 9, 2006

(54) SURFACTANT PREVENTION OF VAGINITIS AND LUNG COMPLICATIONS FROM CANCER CHEMOTHERAPY

(75) Inventors: Joanna Floros, Hershey, PA (US); David S. Phelps, Hershey, PA (US); Colin MacNeill, Hershey, PA (US); Todd M. Umstead, Etters, PA (US); Zhenwu Lin, Hershey, PA (US); Judith Weisz, Bainbridge, PA (US)

(73) Assignee: The Penn State Research Foundation, University Park, PA (US)

( * ) Notice: Subject to any disclaimer, the term of this patent is extended or adjusted under 35 U.S.C. 154(b) by 330 days.

(21) Appl. No.: 10/428,598

(22) Filed: May 2, 2003

(65) Prior Publication Data

US 2003/0225034 A1 Dec. 4, 2003

Related U.S. Application Data

(63) Continuation of application No. 10/317,787, filed on Dec. 12, 2002.

(60) Provisional application No. 60/339,695, filed on Dec. 12, 2001.

(51) Int. Cl.
*A61K 38/00* (2006.01)

(52) U.S. Cl. ........................................................ 514/8

(58) Field of Classification Search ..................... 514/8
See application file for complete search history.

(56) References Cited

U.S. PATENT DOCUMENTS

| | | | |
|---|---|---|---|
| 4,861,756 A | 8/1989 | Jackson | |
| 5,407,914 A | 4/1995 | Cochrane et al. | |
| 5,683,982 A | 11/1997 | McLean et al. | |
| 5,827,825 A | 10/1998 | Takei et al. | |
| 5,891,844 A | 4/1999 | Häfner | |
| 6,013,619 A | 1/2000 | Cochrane et al. | |
| 6,436,970 B1 | 8/2002 | Häfner et al. | |
| 2002/0010494 A1* | 1/2002 | Policker et al. | 607/41 |
| 2002/0072540 A1* | 6/2002 | Larsson et al. | 514/558 |
| 2003/0096975 A1* | 5/2003 | Hostetter et al. | 530/388.5 |

FOREIGN PATENT DOCUMENTS

| | | |
|---|---|---|
| EP | 0733 645 A1 | 9/1996 |
| EP | 0383 837 B1 | 2/1998 |
| EP | 0590 006 B1 | 9/2002 |
| JP | 10316587 A2 | 12/1998 |
| WO | WO 95/32992 A1 | 12/1995 |
| WO | WO 01/76619 A1 | 10/2001 |

OTHER PUBLICATIONS

Chen et al., Surfactant and corticosteroid effects on lung function in a rat model of acute lung injury, Crit Care Med Nov. 2001; 29(11):2169-75 (Abstract).

Hohlfeld et al., The role of pulmonary surfactant in obstructive airways disease, Eur Respir J Feb. 1997; 10(2):482-91 (Abstract).

Otsubo et al., Characterization of synthetic lung surfactant activity against proinflammatory cytokines in human monocytes, Biol Pharm Bull Mar. 2002; 25(3): 312-7 (Abstract).

Wu et al., Effect of surfactant on pulmonary expression of type IIA PLA(2) in an animal model of acute lung injury, Am J Physiol Lung Cell Mol Physiol Apr. 2002; 282(4):L743-50 (Abstract).

Huang et al., Combined SP-A-bleomycin effect on cytokines by THP-1 cells: impact of surfactant lipids on this effect, Am J Physiol Lung Cell Mol Physiol 283:L94-L102, 2002.

\* cited by examiner

*Primary Examiner*—Bruce R. Campell
*Assistant Examiner*—Maury Audet
(74) *Attorney, Agent, or Firm*—McKee, Voorhees & Sease, P.L.C.

(57) ABSTRACT

A means and method for treating pulmonary fibrosis and vaginitis in animals is described. The compositions include surfactant lipids in a pharmaceutically acceptable carrier. Surfactant lipids have been found to suppress the synergistic effect of bleomycin and SP-A in enhancing proinflammatory cytokine production. Surfactant lipids are also effective in the prevention and treatment of pulmonary fibrosis resulting from exposure to inflammatory agents affecting cytokine production. Furthermore, surfactant lipids are effective in treating attenuating the effect of proinflammatory cytokine production in vaginitis.

12 Claims, 7 Drawing Sheets

SEQUENCE LISTING

<160> NUMBER OF SEQ ID NOS: 2

<210> SEQ ID NO 1
<211> LENGTH: 23
<212> TYPE: DNA
<213> ORGANISM: Unknown
<220> FEATURE:
<223> OTHER INFORMATION: oligo-dT primer (sense)

<400> SEQUENCE: 1
gacgtttgtg ttggaagccc tgg                23

<210> SEQ ID NO 2
<211> LENGTH: 24
<212> TYPE: DNA
<213> ORGANISM: Unknown
<220> FEATURE:
<223> OTHER INFORMATION: oligo dT primer (antisense)

<400> SEQUENCE: 2
ggtaccagtt ggtgtagttc acag               24

SURFACTANT PREVENTION OF VAGINITIS AND LUNG COMPLICATIONS FROM CANCER CHEMOTHERAPY

CROSS-REFERENCE TO RELATED APPLICATION

This application is a continuation of application Ser. No. 10/317,787 filed Dec. 12, 2002, which also claims the benefit of U.S. Provisional Application No. 60/339,695, filed Dec. 12, 2001.

GRANT REFERENCE CLAUSE

This invention was funded in part by grants NIH R21 DE-14041, PHS PO1 AI-37829, NIH R21 DE-14041, and NIH 5R37HL-034788-16. The government may have certain rights in this invention.

FIELD OF THE INVENTION

This invention relates to the use of surfactant lipids for a variety of therapeutic uses, including the treatment of pulmonary inflammation and fibrosis, vaginitis, and inflammatory conditions relating to the same.

BACKGROUND OF THE INVENTION

Pulmonary fibrosis (PF) is a complicated, chronic illness characterized by abnormal formation of fiberlike scar tissue in the lungs. Most patients with PF first have alveolitis, or inflammation of the lung, which drives the scarring process. If the disease progresses, the lungs eventually thicken and become stiff, which prevents oxygen from getting from the air sacs into nearby blood vessels that deliver oxygen to the body, thus making it more difficult for the person to breathe.

PF affects each person differently, and progresses at varying rates. Generally, the patient's breathlessness becomes worse over time, and daily activities such as walking, climbing stairs, etc. become more difficult. As the disease advances, the patient may require supplemental oxygen to meet the demands of the body. PF causes hypoxemia, or a lack of oxygen in the blood. This condition may lead to high blood pressure in the lungs (pulmonary hypertension) and put a strain on the heart that can lead to heart dysfunction. PF has also been associated with heart attack, respiratory failure, stroke, pulmonary embolism, and lung infection. In some cases PF can even be fatal.

There are many known causes of PF, including occupational and environmental exposures, sarcoidosis, medications, radiation, connective tissue or collagen diseases such as rheumatoid arthritis and systemic sclerosis, and genetic/familial causes (less common). When all known causes of PF have been excluded, the condition is labeled as idiopathic pulmonary fibrosis (IPF). No matter what the cause, in each case of PF the lung is reacting to some insult by developing inflammation which leads to an exaggerated or uncontrolled healing response that, over time, produces fibrous scar tissue. The histological features of pulmonary fibrosis in human and animal studies include inflammatory cell recruitment, fibroblast proliferation and collagen synthesis. A number of studies concerning the pathogenesis of pulmonary fibrosis have focused on the role of inflammatory cells, especially alveolar macrophages, in the fibrotic process.

Current treatments for PF focus on improving symptoms and slowing progression of the disease. These include administration of corticosteroids to reduce inflammation, which are often used in combination with a drug to suppress the body's immune response, such as azathioprine or cyclophosphamide. Unfortunately, this treatment approach improves symptoms and/or improves the life span only some of the time. These drugs can also cause numerous side effects, some of which are severe. Interferon gamma-Ib is a new drug shown to be superior to corticosteroids in preliminary studies. However, its current cost (approximately $100,000/year) is prohibitive for most patients.

In advanced cases of PF, doctors may consider lung transplantation. This procedure is most often performed in patients under 60 years of age whose PF has been unresponsive to other treatments. However, lung transplantation is extremely invasive and expensive, and often requires patients to wait months to years until matching organs become available. Further, many patients are ineligible for transplantation.

There is therefore a need in the art for a new method and means of treating PF that overcomes at least some of the disadvantages associated with current treatments.

As noted above, certain medications are associated with the development of pulmonary fibrosis, including nitrofurantoin, amiodarone, and the chemotherapeutic agents bleomycin, cyclophosphamide, and methotrexate. Bleomycin is a group of glycopeptides isolated from *Streptomyces verticillus*. Although it is an effective antineoplastic agent, bleomycin-induced pulmonary fibrosis can become fatal and therefore limits the usefulness of the drug. Bleomycin has a differential effect on pulmonary fibrosis. Evidence suggests that there is an individual susceptibility in pulmonary fibrosis, and genetic factors are implicated in the pathogenesis of fibrosis to explain variation in susceptibility. Bleomycin induces inflammatory cells from human and animal lung to secrete multifunctional cytokines, such as TNF-$\alpha$, IL-1$\beta$, IL-8, and TGF-$\beta$.

The mechanism of bleomycin-induced cytokine production is not well understood. The cytotoxic effect of bleomycin is believed to be related to DNA damage that is characterized by the appearance of DNA damage-inducible proteins and apoptosis. There is also increased activity of NF-kB, which may result from the increase of reactive oxygen species by bleomycin. NF-kB is a transcriptional factor that regulates the expression of many cytokine genes. Among these, TGF-$\beta$ is considered to be an important cytokine related to fibroblast proliferation and collagen synthesis and TNF-$\alpha$ is considered to be a central mediator in bleomycin-induced pulmonary fibrosis. TNF-$\alpha$ receptor knockout mice have been shown to be protected from pulmonary injury following exposure to bleomycin.

Pulmonary surfactant is essential for normal lung function. The primary function of pulmonary surfactant is to reduce surface tension at the air-liquid interface of the alveolus, which in turn prevents lung collapse at low lung volumes.

Surfactant protein A (SP-A), in addition to surfactant-related function, plays a role in local host defense and regulation of inflammatory processes in the lung. Moreover, SP-A regulates cytokine expression by alveolar macrophages (i.e. IL-1, TNF-$\alpha$ etc.) and expression of SP-A itself is regulated by cytokines (such as IFN-$\gamma$). SP-A also stimulates fibroblasts to produce collagen, and may affect cytokine expression by lung fibroblasts.

SP-A is a collagenous C-type lectin or collectin and its carbohydrate recognition domain (CRD) is involved in binding SP-A to pathogens and promoting phagocytosis of these pathogens by the macrophages. In the macrophage-like THP-1 cell line, human SP-A stimulates production of TNF-α, IL-1β, IL-8, and IL-6 in a dose- and a time-dependent manner. SP-A-enhanced TNF-α production appears to involve NF-kB activation. SP-A also enhances immune cell proliferation and increases expression of some cell surface proteins. In addition, SP-A knockout mice show an increased susceptibility to infection. A recent in vivo study suggests a role for SP-A in neutrophil recruitment into the lungs of preterm lambs.

Surfactant lipids (surfactant TA) can modulate adherence and superoxide production of neutrophils. Surfactant lipids inhibit several SP-A regulated immune cell functions, including stimulation of macrophages. Surfactant lipids and SP-A may be counterregulatory and changes in the relative amounts of surfactant lipids to SP-A may be important in determining the immune status of the lung. Although most of SP-A in the normal alveolar space is thought to be lipid-associated, "lipid-free" SP-A could increase if the balance between SP-A and surfactant lipid was altered under certain conditions.

The present inventors have now found that SP-A plays a role in bleomycin-induced fibrosis, by affecting cytokine expression and/or collagen production. It has further been discovered that "lipid-free" SP-A, the result of an imbalance of SP-A and surfactant lipids following bleomycin treatment, may enhance the effect of bleomycin on proinflammatory cytokine production, and may be partly responsible for bleomycin-induced pulmonary fibrosis. Based on these findings, the present inventors have now determined that the administration of surfactant lipids is effective in suppressing the pulmonary inflammatory processes induced by bleomycin or other causative agents, thereby preventing PF.

Infectious vaginitis is the most common reason that women present for healthcare with a gynecologic condition, accounting for ten million visits per year in the United States. The impact of vaginitis on health outcomes is large, and affects women of every reproductive age, ranging from major pregnancy complications and preterm labor, to infertility, post-operative infection, and increases susceptibility to sexually transmitted diseases (STDs).

There are estimated to be six million cases of bacterial vaginosis (BV) per year in the United States, half of which are without symptoms. Characterized by a shift in vaginal microbes toward a predominance of anaerobic species, BV is the most frequently encountered form of vaginitis. The substantial impact of vaginitis on several important women's health disorders is increasingly coming to light. For example, in both symptomatic and asymptomatic forms, vaginitis has been shown in multiple studies to be highly associated with preterm birth. Importantly, while standard treatment in pregnancy will resolve the vaginitis, the incidence of preterm birth is not reduced by vaginitis detection and treatment protocols carried out in an otherwise low risk population. While the activation of the vaginal immune response has been thought to be a critical determinant of adverse outcomes in women with BV, the mechanism by which vaginal immunity becomes active has been previously unknown.

The present inventors have also surprisingly discovered that SP-A is expressed in the vaginal mucosa and is present in vaginal lavage find. Based upon this finding, the inventors speculate that administration of surfactant lipids is also effective in decreasing proinflammatory cytokines in women, thereby preventing or reducing the symptoms of vaginitis, and preventing complications resulting from vaginitis, such as preterm labor.

It is therefore a primary objective of the present invention to provide a means of preventing and/or treating pulmonary fibrosis.

It is another objective of the present invention to provide a means of preventing and/or treating bleomycin-induced pulmonary fibrosis.

It is a further objective of the present invention to provide a means of preventing and/or treating pulmonary fibrosis through the administration of surfactant lipids.

It is still a further objective of the present invention to provide a means of preventing and/or treating pulmonary fibrosis that is more effective than previously available treatments for PF.

It is a yet a further objective of the present invention to provide a means of preventing and/or treating pulmonary fibrosis that has a lesser degree of side effects than previously available treatments for PF.

It is a further objective of the present invention to provide a method and means of preventing and/or treating vaginitis.

It is still a further objective to provide a method and means of preventing and/or treating vaginitis through the administration of surfactant lipids.

It is a further objective of the present invention to provide a method and means of preventing complications that arise from vaginitis, such as preterm labor, infertility, post-operative infection, and STDs.

These and other objectives will become clear from the foregoing detailed description.

SUMMARY OF THE INVENTION

The present invention is directed to a method and means for preventing and treating pulmonary fibrosis (PF) through the administration of surfactant lipids. The invention is based on the finding that both SP-A and bleomycin stimulate production of inflammatory cytokines, and that there is a synergistic effect when both agents are used. The significantly elevated cytokine levels resulting from this synergism appear responsible for pulmonary fibrosis. It has surprisingly been found that administration of surfactant lipids significantly suppress the synergistic effect of SP-A/inflammatory agents on cytokine production. This finding may in turn be used in the prevention and treatment of pulmonary complications observed during chemotherapy, as well as in general prevention and treatment of PF.

The present invention is also directed to a method and means for preventing and treating vaginitis through the administration of surfactant lipids. Suppression of the inflammatory symptoms of vaginitis will help prevent short-term and long-term complications arising from the disease, such as preterm labor, infertility, post-operative infection, and STDs.

DETAILED DESCRIPTION OF THE INVENTION

Figure 1A:
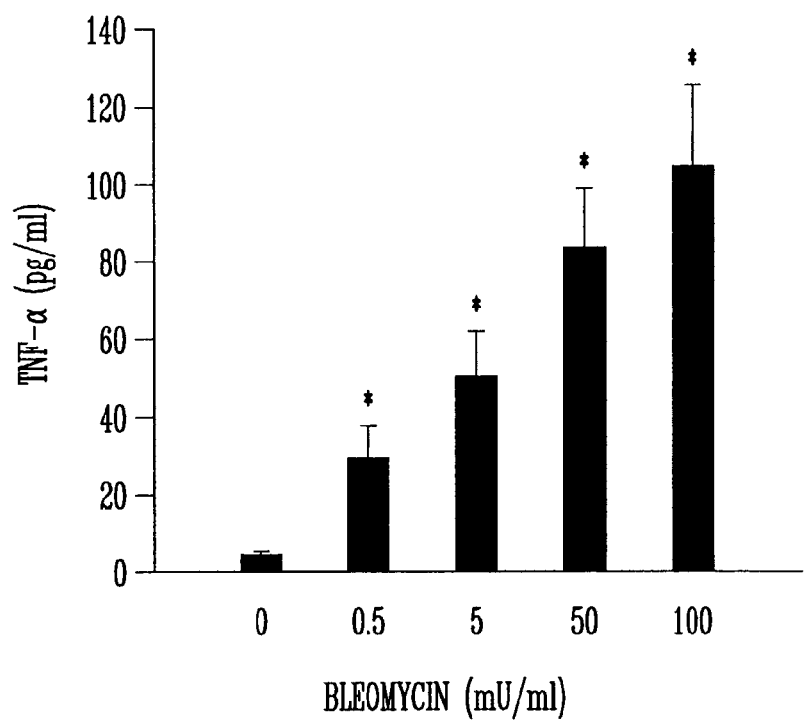
FIG. 1 illustrates dose-response cytokine production after bleomycin treatment by THP-1 cells, a human cell line used to serve as a model for lona macrophages. Differentiated THP-1 cells were stimulated with the indicated concentration of bleomycin for 4 h or 6 h. TNF-α (Panel A) and LL-8 (Panel B) levels in culture medium at 4 h incubation and IL-1β(Panel C) at 6 h were quantified by ELISA. The effect of Ara-C, a chemotherapeutic agent that does not cause PF, on TNF-α was examined at 4 h (panel D). Data are derived from 5 separate experiments except the Ara-C experiments which are from two experiments in triplicate. Results are given as means ± SEM. The indicated values (*) are significantly different (p<0.05) from points obtained in the absence of bleomycin.
Figure 1B:
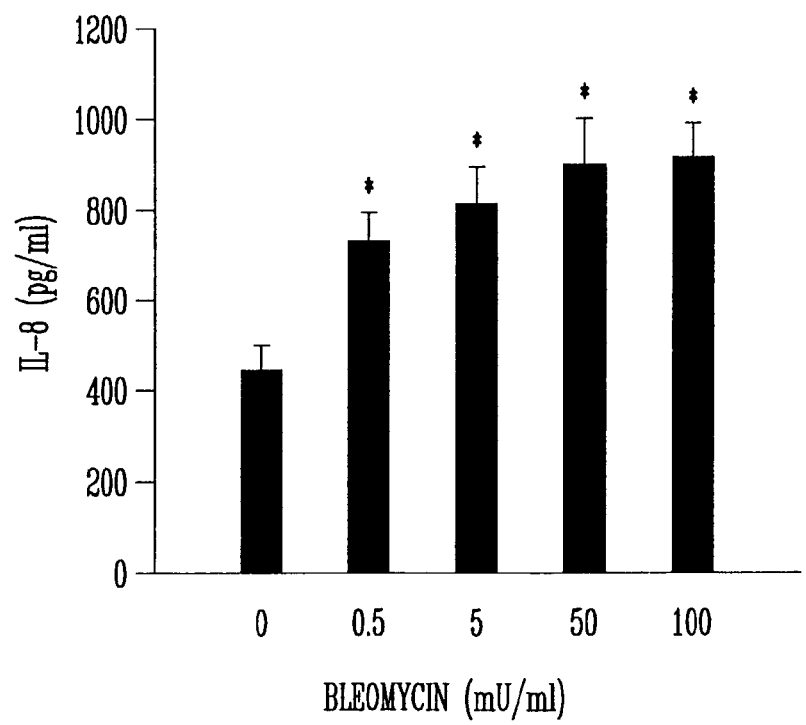
Figure 1C:
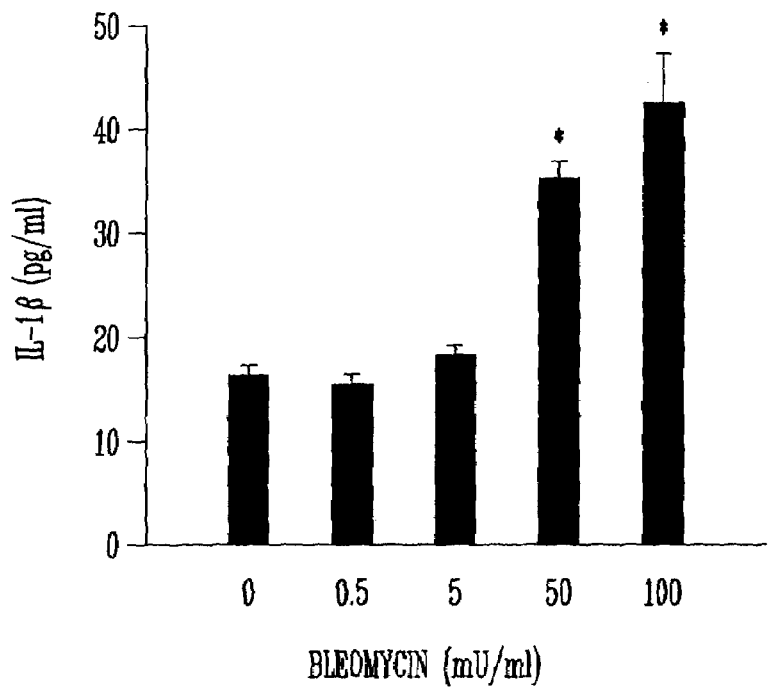
Figure 1D:
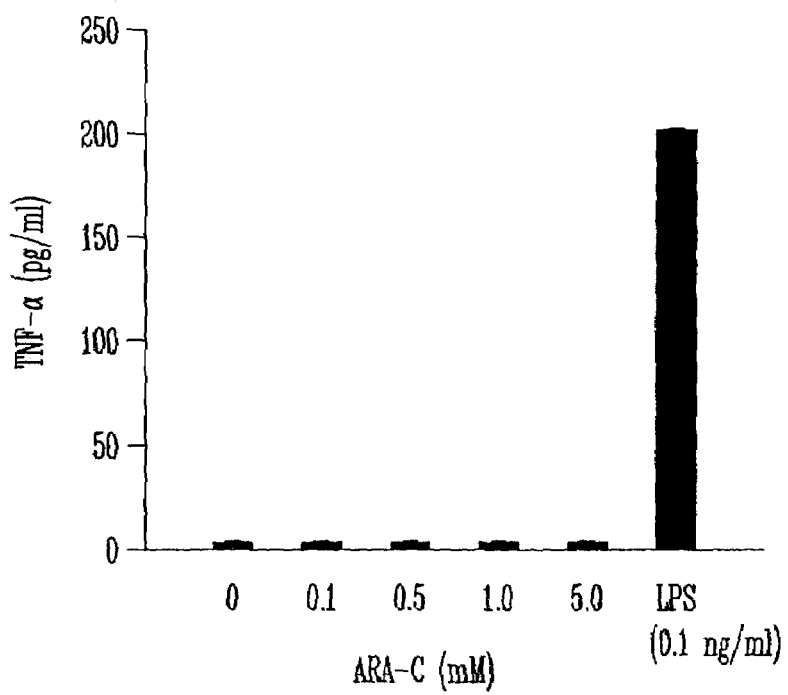

The present invention relates to the discovery that SP-A plays a role in bleomycin-induced fibrosis by affecting cytokine expression and/or collagen production. The invention is premised on the finding that surfactant lipids significantly suppress the additive or synergistic effect on cytokine production observed in the presence of both SP-A and bleomycin, or other causative factors associated with lung inflammation and fibrosis.

It should be understood that while the invention is specifically described in terms of pulmonary inflammation and fibrosis as a result of treatment with bleomycin, the invention is also effective in treating pulmonary inflammation and fibrosis resulting from other lung inflammatory agents. These agents include, but are not limited to nitrofurantoin, amiodarone, cyclophosphamide, and methotrexate, as well as other known and unknown causes.

While not wishing to be bound by any theory, it is believed that treatment with bleomycin or exposure to other inflammatory agents causes a substantive change in the patient's lung surfactant, which in turn enhances the stimulatory influence of SP-A. Under normal physiological conditions, most of the SP-A in the alveoli is combined with surfactant lipids in the form of a surfactant lipoprotein complex. It appears that these SP-A/lipid complexes do not affect cytokine production, perhaps because the complexed SP-A is unable to interact directly with immune cells. Therefore, it is possible that if the lipids are reduced in quantity or quality, the stimulatory influence of SP-A is enhanced. In fact, results in animal models have demonstrated that bleomycin-induced pulmonary fibrosis causes changes in surfactant composition and function. Studies in rats indicate there is a significant increase in SP-A but not of surfactant phospholipids in response to bleomycin. It has also been shown that although surfactant lipids by themselves have no effect on cytokine production, surfactant lipids completely inhibit SP-A proinflammatory function observed in both, ELISA and RPA assays of cytokine protein and mRNA, respectively. Thus, surfactant lipids can significantly inhibit the combined effects of SP-A and inflammatory agents on cytokines.

The present invention also relates to the surprising finding that SP-A is present in human vaginal mucosa and secreted into the vaginal tissue phase. By immunocytochemistry, SP-A immunoreactivity has been localized in two discrete layers of the vaginal epithelium: (1) the deep intermediate layer, where differentiated epithelial cells are localized, and; (2) the superficial layer, comprised of dead epithelial cells, where SP-A is likely to be extracellular and associated with a glycocalyx. Transcripts of SP-A, identical in size to that in lung, were identified by Northern analysis in RNA isolated from vaginal wall and shown, by sequencing of RT/PCR products, to be derived from each of the two closely related SP-A genes, SP-A1 and SPA2. The presence of SP-A in vaginal lavage fluid has been demonstrated by two-dimensional gel electrophoresis, followed by mass spectrometry of the protein isolated from the gel.

The knowledge that SP-A is present and probably serves a host-defense function in the vagina led to the speculation that administration of surfactant lipid may be used to treat the vaginitis-induced inflammatory response. More specifically, surfactant lipid has been shown to balance the proinflammatory properties of the innate immune protein, SP-A. SP-A has a well-demonstrated ability to enhance the production of several mediators of inflammation. This enhanced production may be attenuated by administration of surfactant lipids.

It has also been found that in the vagina of normal, healthy, reproductive age women, the same mediators of inflammation, IL-1β and IL-8 are significantly increased in the follicular phase of the monthly cycle. Importantly, SP-A is increased significantly in vaginal fluid at the same time of the month that IL-1β and IL-8 are increased. It is therefore believed that elevated amounts of SP-A in the vagina are causally associated with an increased inflammatory potential that is marked by proinflammatory cytokines. It is moreover believed that this increased inflammatory potential is attenuated by instilling surfactant lipid in the vagina.

Reduction of vaginitis-associated inflammation has broad applications. For instance, a daunting obstetrical problem, the incidence of preterm labor and delivery (PTL) has increased from 8% to 11.7% in the last 14 years. At least 30% of PTL is thought to involve ascending infection from the lower genital tract, and BV confers a three-fold risk of PTL. In a pilot group of pregnant patients found to be in PTL, there is preliminary evidence that SP-A levels are increased five-fold over gestational-age matched controls, and this increase corresponds with a three-fold increase in IL-1β. While antibiotic treatment of vaginitis in a low-risk population (i.e., without a prior PTL) does not decrease the rate of PTL, administration of surfactant lipids with or without oral antibiotics is expected to decrease the incidence of PTL. Because BV complicates 20% of pregnancies, the impact of this finding on women's health would be tremendous.

There are several other potential applications for administration of surfactant lipids with respect to women's health disorders. For example, female pelvic surgeries are known to be complicated by a substantially increased rate of post-operative pelvic infection in women with vaginitis. Treatment of vaginitis preoperatively has been shown to decrease the rate of post-operative infection by an approximate average of only about 40%. It is likely that surfactant lipids alone or preferably in combination with antibiotic therapy would yield a significantly improved decrease in post-operative pelvic infection. Other examples of women's health conditions adversely affected by vaginitis range from infertility to upper genital tract infection/endometritis to increased risk of STDs. It is anticipated that these conditions would also enjoy an improved outcome using therapeutic regimens of surfactant lipids and/or antibiotic therapy.

Further, until now, in vivo studies of SP-A function, including those investigating SP-A/surfactant lipid interactions, were limited by the experimental systems available. For example, human studies often require lung lavage, an invasive procedure wherein lavage dilutions are difficult to control, and murine systems differ diverge from human systems in important ways, i.e. there is a single murine SP-A gene, while human SP-A is encoded by two linked genes, SP-A1 and SP-A2. Given these considerations, the vaginal mucosa is readily accessible by relatively non-invasive methods. Thus, it offers a valuable system for investigations of the role of SP-A as well as of other putative mediators of local host defenses.

The human SP-A locus is located on the large arm of chromosome 10 and consists of two functional genes and one pseudogene. The order for the SP-A sequences from the centromere to the telomere is as follows: SP-A2, pseudogene, and SP-A1. The transcriptional orientation of the SP-A2 and pseudogene is opposite to that of SP-A1. As discussed above, SP-A plays a role in bleomycin induced fibrosis, by affecting cytokine expression and/or collagen production. Functional differences exist among the various SP-A alleles with regard to their ability to induce cytokine expression and/or collagen production by alveolar macrophages and/or lung fibroblasts. These differences may explain in part the individual variability observed in the susceptibility of fibrosis among individuals.

Although the mechanism of action of SP-A in cytokine production is not known, it is likely that it involves interaction with a cell membrane molecule, possibly the C1q receptor, activating intracellular events including the eventual activation of NF-kB. When SP-A and bleomycin are added to the cell at the same time, the levels of both TNF-α and IL-8 have been found to be higher than the sum of each cytokine induced by SP-A or bleomycin alone. Analysis of mRNA shows that the combined treatment of SP-A and bleomycin exhibits an additive effect on the expression of TNF-α, IL-1β, and IL-8 mRNA. Although bleomycin itself does not induce a significant increase of IL-1β mRNA, it greatly enhances the level of IL-1β mRNA after being combined with SP-A. The fact that the combined effect of SP-A+bleomycin shown in cytokine protein production is much greater than that observed in mRNA level indicates that various post-transcriptional and post-translational mechanisms may be involved in bleomycin-induced proinflammatory cytokine production by THP-1 cells in response to SP-A.

As used herein, the terms "surfactant lipids" or "surfactant TA" are defined as natural or artificial substances composed of phospholipids, neutral lipids, and hydrophobic surfactant-associated proteins B and C(SP-B and SP-C) capable of forming a layer between the alveolar surface and the alveolar gas and reducing alveolar collapse by decreasing surface tension within the alveoli. Current commercially available surfactant lipids are derived from human, animal (bovine), or synthetic sources, and may be purchased under the trade names Infasurf® (calfactant), Exosurf® (surfactant, synthetic), Curosurf®, and Survanta® (beractant). However, persons skilled in the art can readily appreciate that various other brands and types of surfactant from various sources that may become available in the future are also appropriate for use in this invention.

The surfactant lipids of the present invention may be generally used for the prophylaxis and treatment of pulmonary fibrosis, vaginitis, and other female reproductive disorders as discussed above. The surfactant lipids are administered along with a pharmaceutically acceptable carrier. Any pharmaceutically acceptable carrier may be generally used for this purpose, provided that the carrier does not significantly interfere with the stability or bioavailability of the surfactant lipid compounds of this invention. Examples of such carriers and methods of formulating such carrier may be found in Remington's Pharmaceutical Sciences.

The surfactant lipids of this invention can be administered in any effectively pharmaceutically acceptable form to warm blooded animals, including human and other animal subjects, e.g. in topical, lavage, oral, suppository, parenteral, or infusible dosage forms, as a topical, buccal, sublingual, nasal spray, vaginally suppositories, vaginal infusions, vaginal creams, vaginal tablets, or in any other manner effective to deliver the agents. The route of administration will preferably be designed to optimize delivery and/or localization of the agents to target cells. Although to date surfactant lipids are conventionally administered intratracheally, persons skilled in the art can readily appreciate that other forms of administration may be suitable as well.

In addition to the active compounds i.e. the surfactant lipids, the pharmaceutical compositions of this invention may contain suitable excipients and auxiliaries which facilitate processing of the active compounds into preparations which can be used pharmaceutically. Oral dosage forms encompass tablets, capsules, and granules. Preparations which can be administered rectally include suppositories. Other dosage forms include suitable solutions for administration parenterally, intratracheally, intravaginally, intranasally, or orally, and compositions which can be administered buccally or sublingually.

The pharmaceutical preparations of the present invention are manufactured in a manner which is itself well known in the art. For example the pharmaceutical preparations may be made by means of conventional mixing, granulating, dissolving, lyophilizing processes. The processes to be used will depend ultimately on the physical properties of the active ingredient used.

Suitable excipients are, in particular, fillers such as sugars for example, lactose or sucrose mannitol or sorbitol, cellulose preparations and/or calcium phosphates, for example, tricalcium phosphate or calcium hydrogen phosphate, as well as binders such as starch, paste, using, for example, maize starch, wheat starch, rice starch, potato starch, gelatin, gum tragacanth, methyl cellulose, hydroxypropylmethylcellulose, sodium carboxymethylcellulose, and/or polyvinyl pyrrolidone. If desired, disintegrating agents may be added, such as the above-mentioned starches as well as carboxymethyl starch, cross-linked polyvinyl pyrrolidone, agar, or alginic acid or a salt thereof, such as sodium alginate. Auxiliaries are flow-regulating agents and lubricants, for example, such as silica, talc, stearic acid or salts thereof, such as magnesium stearate or calcium stearate and/or polyethylene glycol. Oral dosage forms may be provided with suitable coatings which, if desired, may be resistant to gastric juices.

For this purpose concentrated sugar solutions may be used, which may optionally contain gum arabic, talc, polyvinylpyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethylcellulose phthalate, dyestuffs and pigments may be added to the tablet coatings, for example, for identification or in order to characterize different combination of compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, liquid paraffin, or liquid polyethylene glycols. In addition stabilizers may be added. Possible pharmaceutical preparations which can be used rectally include, for example, suppositories, which consist of a combination of the active compounds with the suppository base. Suitable suppository bases are, for example, natural or synthetic triglycerides, paraffin hydrocarbons, polyethylene glycols, or higher alkanols. In addition, it is also possible to use gelatin rectal capsules which consist of a combination of the active compounds with a base. Possible base materials include for example liquid triglycerides, polyethylene glycols, or paraffin hydrocarbons.

Suitable formulations for parenteral, intravaginal, or intratracheal administration include aqueous solutions of active compounds in water-soluble or water-dispersible form. In addition, suspensions of the active compounds as appropriate oily injection suspensions may be administered. Suitable lipophilic solvents or vehicles include fatty oils for example, sesame oil, or synthetic fatty acid esters, for example, ethyl oleate or triglycerides. Aqueous injection suspensions may contain substances which increase the viscosity of the suspension, including for example, sodium carboxymethyl cellulose, sorbitol and/or dextran. Such compositions may also comprise adjuvants such as preserving, wetting, emulsifying, and dispensing agents. They may also be sterilized, for example, by filtration through a bacteria-retaining filter, or by incorporating sterilizing agents into the compositions. They can also be manufactured in the form of sterile solid compositions which can be dissolved or suspended in sterile water, saline, or other injectable medium prior to administration.

In addition to administration with conventional carriers, active ingredients may be administered by a variety of specialized delivery drug techniques which are known to those of skill in the art, such as portable infusion pumps.

The surfactant lipid compositions of the present invention are administered along with a pharmaceutically acceptable carrier in an amount sufficient to prevent pulmonary fibrosis or vaginitis, and/or treat active cases of the diseases. The surfactant lipid compounds of this invention have extremely low toxicity and a low degree of side effects even at high doses. The dosing range of the surfactant lipid compositions will vary depending on a number of factors, such as whether it is used for prophylaxis or treatment of active disease, route of administration, dosing schedule, etc.

As a general guideline, the therapeutic dose of surfactant lipids may range between about 30–800 mg/kg. However, persons skilled in the art can readily appreciate that lower or higher doses of surfactant may be appropriate depending on a number of factors, including cost, severity of the disease, etc. The foregoing doses may be administered as a single dose or may be divided into multiple doses for administration. The surfactant lipid compositions may be administered once to several times daily.

For prevention of PF, a typical dosing schedule could be, for example, 30–800 mg/kg weekly beginning 1–2 weeks prior to exposure to a pulmonary inflammatory agent, such as bleomycin, until 1–2 weeks post-exposure.

For prevention and treatment of vaginitis, a preferred dosing range of surfactant lipids would be from about 1–5 mg as a one time dose, with a preferred dose of about 1.6–4.8 mg, and a most preferred dose of about 3.2 mg. This dose may or may not be repeated. Persons skilled in the art can appreciate that higher or lower doses may be appropriate depending on certain other factors, for example, severity and length of infection, history of prior infections, etc.

Surfactant lipids may also be used in the prevention of preterm labor in women at increased risk, which may represent up to 8–10% of all pregnancies. Risk factors for preterm labor are well known in the art and include, but are not limited to, multiple pregnancy (expecting twins or more), presence of uterine fibroids or other uterine abnormalities, vaginal bleeding in the second or third trimester, smoking or other substance use, maternal age of less than 20 or more than 35, low pre-pregnancy weight, low weekly weight gain, nulliparity, previous preterm birth, histories of two or more induced abortions, spontaneous abortions or stillbirths, uterine exposure to diethylstilbestrol (DES), incompetent cervix, uterine anomaly, and pyelonephritis. In women that have one or more risk factors present for preterm labor, surfactant lipids could be administered, for example, during each of weeks 20–34 of the pregnancy in the doses described above, with or without another agent for treating vaginitis, such as an antibiotic or antifungal agent as described in more detail below.

Fur purposes of treating vaginitis and/or preventing preterm labor caused by vaginitis, the surfactant lipids of this invention are preferably administered in conjunction with one or more medications used to treat vaginitis, including antibiotics and antifungals. Any medications that are normally used in the treatment of vaginitis are appropriate for this purpose. Suitable antibiotics include, but are not limited to, ampicillin, ceftriaxone, clindamycin, metronidazole, and tetracycline. Suitable antifungals include, but are not limited to, miconazole, clotrimazole, econazole, butoconazole, tioconazole, and terconazole. These and other vaginitis medications should be administered in their usual dosages/dosing schedules/route of administration for treating vaginitis. An example of a preferred drug regimen for treating BV would include one-time intravaginal administration of 3.2 mg of surfactant lipids, along with 500 g of metronidazole, two times a day for 7 days.

In addition, surfactant lipids may be used to treat various other female diseases and disorders. For instance, surfactant lipids may be administered with or without antibiotics, antifungal agents, and/or other antiinflammatory drugs to decrease post-operative pelvic infection, infertility, and reduce the risk of STDs. Preferred dosages, routes of administration, etc. are as set forth above for treatment of vaginitis.

The following examples are offered to illustrate but not limit the invention. Thus, it is presented with the understanding that various formulation modifications as well as method of delivery modifications may be made and still are within the spirit of the invention.

EXAMPLE 1

Effects of SP-A on Bleomycin-Induced Cytokine Production and mRNA Expression in THP-1 Cells Materials and Methods Cell Culture The THP-1 cell line was obtained from the American Type Culture Collection. Cells were grown in RPMI 1640 medium (Sigma) with 0.05 mM 2-mercaptoethanol containing 10% fetal calf serum (FCS; Summit Biotechnology) at 37° C. in an atmosphere of 5% $CO_2$. The cells were split periodically and used at passages 8–15 in the various experiments. After differentiation with $10^{-8}$ M Vitamin $D_3$ for 72 h, cells were pelleted and washed with cold PBS. The cell pellet was then resuspended in complete RPMI 1640 medium with 10% FCS at a density of $2 \times 10^6$ cells/ml in 24-well culture plates, and exposed to bleomycin and SP-A. Cell viability was determined by trypan blue exclusion. Under the conditions employed in this study, neither bleomycin nor SP-A appeared to have any effect on the viability of THP-1 cells. Incubations were terminated by pelleting the cells. Supernatants and/or cell pellet were stored at −80° C. until assayed.

Bleomycin and Native Human SP-A

Bleomycin (Blenoxane; Bristol-Myers Squibb Co) solutions were prepared immediately before use with endotoxin-free saline (American Pharmaceutical Partners, Inc.). Lipopolysaccharide (LPS) was not detected in the stock solution of bleomycin at a bleomycin concentration of 5 U/ml (1U=1 mg) using the method described below.

SP-A was purified from bronchoalveolar lavage of alveolar proteinosis patients with 1-butanol extraction. After extraction of whole surfactant with butanol, the pellet was completely dried with a flux of nitrogen gas and then homogenized twice in a freshly prepared buffer (20 mM n-Octyl β-D-Glucopyranoside, 10 mM HEPES, 150 mM NaCl, pH 7.4). After pelleting, the insoluble protein was dissolved in 5 mM Tris-HCl, pH 7.5 and dialyzed for 48 h against the same buffer. The dialyzed solution was centrifuged (210K×g, 4° C., 30 min) and the supernatant containing SP-A was collected and stored at -80° C. The purified protein was examined by two-dimensional gel electrophoresis followed by western blotting and silver staining, and was found to be greater than 98% pure. Protein concentration was determined with the micro bicinchoninic acid method (Pierce) with RNAse A as a standard. SP-A was stored at −80° C. Endotoxin content was determined with the QCL-1000 Limulus amebocyte lysate assay (Biowhittaker). This test indicated that the SP-A used contained <0.1 pg LPS/10 μg SP-A.

Stimulation of THP-1 Cells with SP-A and Bleomycin

After differentiation with $10^{-8}$ M of vitamin $D_3$ for 72 h, THP-1 cells were pelleted and washed as described above. Cells at a density of $2 \times 10^6$ cells/ml were incubated at 24 well culture plates. For dose-response study, cells were stimulated with bleomycin at concentrations ranging from 0–100 mU/ml. Time-dependent secretion of cytokines following bleomycin treatment was studied from 0–24 h with 5 and 50 mU/ml of bleomycin. In experiments where the combined effects of SP-A and bleomycin were examined, SP-A (10 μg/ml) and bleomycin (5 or 50 mU/ml) were added to cells simultaneously, unless otherwise noted. After treatment, the culture medium was collected at 4 h or 6 h for the ELISA assay of cytokine production and cells were harvested at 2 h or 4 h for cytokine mRNA analysis.

Cytosine arabinoside (Ara-C, Cytosar-U, Pharmacia & Upjohn) was included in some experiments to confirm the specificity of the effect of bleomycin on proinflammatory cytokine production by THP-1 cells. Ara-C is another antineoplastic agent with known cytotoxicity. Although it has not been associated with pulmonary fibrosis and cytokine production, it has been shown to cause non-cardiogenic pulmonary edema. Ara-C, at concentrations ranging from 0.1 to 5 mM in culture medium, was used for evaluating the effect of Ara-C on TNF-α. The conditions employed in the Ara-C experiments were the same as those in bleomycin studies except that only a 4 h time point was done.

Infasurf Inhibition of Cytokine Production

Infasurf (Forest Pharmaceuticals), an extract of natural surfactant from calf lung, was used as a source of surfactant lipid. Infasurf was supplied by the manufacturer as a suspension containing 35 mg phospholipids/ml of sterile saline. Infasurf is predominately phosphatidylcholine and contains ~2% wt/wt protein that includes SP-B and SP-C, but no SP-A. Infasurf in concentrations ranging from 100 to 800 μg/ml was used in the experiments for ELISA assay of cytokine production, but only a single dose (400 μg/ml) of Infasurf was used in the experiment for mRNA analysis. Infasurf was preincubated separately with SP-A (10 μg/ml), bleomycin (5 mU/ml), and SP-A+bleomycin for 15 min at 37° C. before addition to the THP-1 cells. Cells were incubated for 4 h after the treatment. Culture medium and cell pellets were then collected for ELISA assay and mRNA analysis, respectively.

ELISA Assay

The ELISA assays for TNF-α, IL-8, and IL-1β (OptEIA Human ELISA Sets, Pharmingen) were performed according to the instructions recommended by the manufacturer. The ELISA kits were capable of measuring levels of 7.8–500 pg/ml for TNF-α, 6.2–400 pg/ml for IL-8 and 20–1000 pg/ml for IL-1β. A reference curve for each of these cytokines was obtained by plotting the concentration of several dilutions of standard protein versus the corresponding absorbance.

Analysis of Cytokine mRNA

Total RNA was isolated from THP-1 cells at 2 h or 4 h after treatment by using Rneasy Mini Kits (QIAGEN) according to the protocol of the RNeasy Mini Handbook. Cytokine mRNA quantification was performed by ribonuclease protection assay (RPA). RiboQuant™ Ribonuclease RPA Starter Package and a Customized Human Template Set (Pharmingen) were used to analyze TNF-α, IL-1β, and IL-8 mRNA in one assay. The customized template set contains DNA templates that can be used for T7 RNA polymerase-directed synthesis of α-$^{32}$P-UTP-labeled, anti-sense RNA probes. These can be hybridized to TNF-α, IL-1β, and IL-8 mRNA. Templates for the L32 and GAPDH housekeeping genes were also included to allow for normalization of sampling or technical error. Aliquots of 2 μg of total RNA were hybridized with radiolabeled probes at 56° C. for 16 h. RNase treatment followed, resulting in degradation of single-stranded RNA and free probes. After inactivation and precipitation, protected probes were resolved by a 5% polyacrylamide-urea sequence gel electrophoresis and visualized by autoradiography. Densities of the protected bands were quantified by soft laser densitometry. The mRNA level is expressed as the ratio of the densitometric value of each cytokine mRNA to that of the L32 or GAPDH mRNA.

Statistics

Values are presented as means±SEM. Data were analyzed using SigmaStat statistical software. For each experiment, statistical treatment included a one-way analysis of variance (ANOVA) followed by a Student-Newman-Keuls test for pairwise comparison and was judged to be significantly different at $p<0.05$.

Results

Dose-Response and Time Course Studies of Bleomycin Effects on Stimulation of Cytokine Production by THP-1 Cells To study the response of THP-1 cells to bleomycin stimulation, a dose-response and a time course of bleomycin effects on TNF-α, IL-1β, and IL-8 levels was performed. The concentrations of bleomycin for the dose-response study ranged from 0–100 mU/ml, which spans a relevant pharmacological dose. As shown in FIG. 1, a bleomycin concentration as low as 0.5 mU/ml increased both TNF-α and IL-8 levels (panels A and B), but a higher concentration of bleomycin (50 mU/ml) was needed to increase the IL-1β level significantly (panel C). Cytokine production continued to increase as the bleomycin dose was increased to 100 mU/ml. In contrast, the TNF-α even after Ara-C treatment did not differ from that of control (panel D).

Figure 2A:
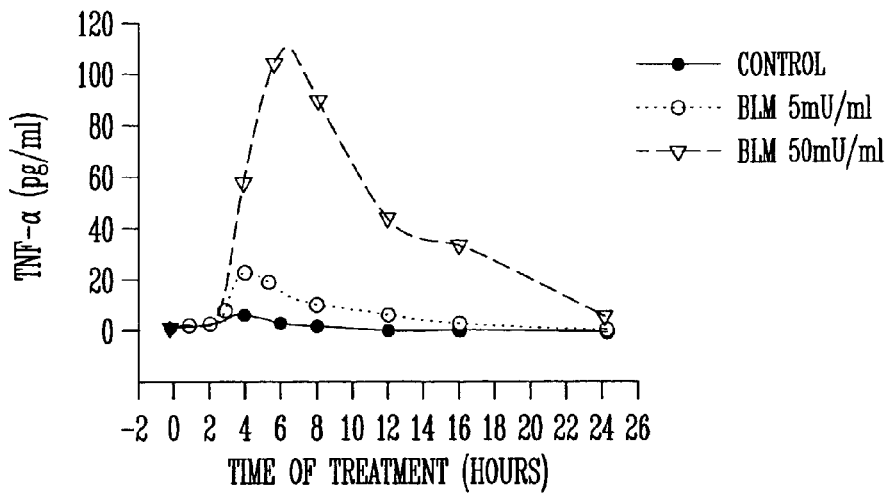
FIG. 2 illustrates the time course of cytokine production after bleomycin treatment. Differentiated THP-1 cells were incubated in the presence of 0, 5, 50 mU/ml bleomycin for the indicated time. TNF-α (Panel A), IL-8 (Panel B) and IL-1β (Panel C) levels in culture medium were quantified by ELISA.
Figure 2B:
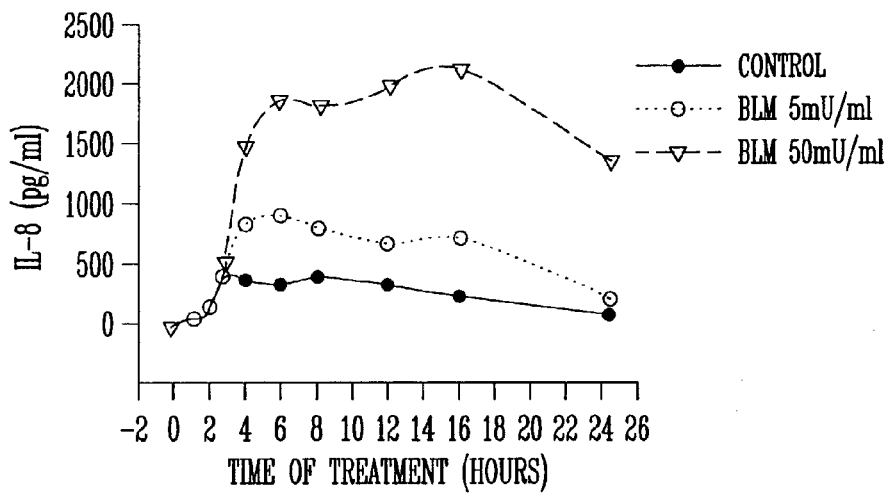
Figure 2C:
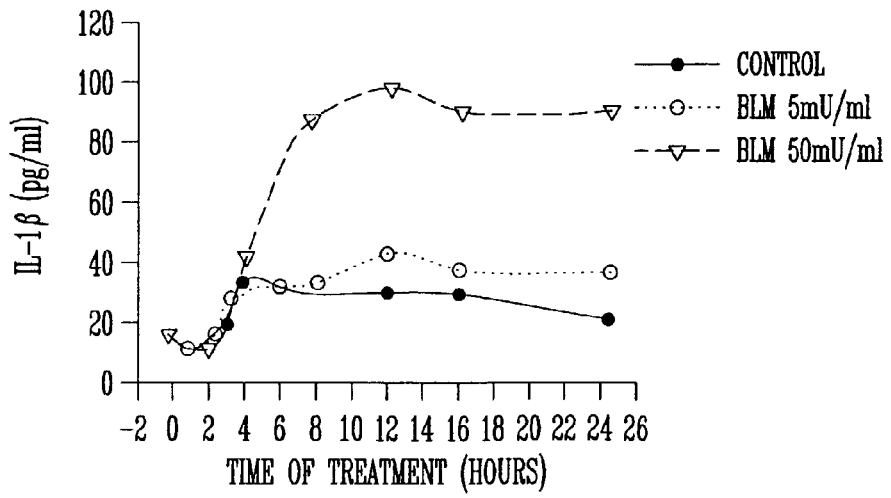

FIG. 2 illustrates the time-dependent secretion (0–24 h) of TNF-α, IL-1β, and IL-8 by THP-1 cells in the presence or absence of different bleomycin doses. The basal level of TNF-α at 0h (starting point) was low. The increase of TNF-α levels was usually detected at 3 h following bleomycin treatment and quickly reached a maximum by 4 to 6 h depending on the dose selected (FIG. 2A). The content of TNF-α subsequently decreased and returned to background levels at 24 h. Initially, IL-8 had a similar response pattern to TNF-α, with respect to its increase and peak response time, but after reaching maximal level at around 5 h, IL-8 didn't show a significant decline until 24 h (FIG. 2B). The level of IL-1β increased much later (FIG. 2C) than that of TNF-α and IL-8, and reached a peak at 10 h after bleomycin treatment. Unlike that of TNF-α and IL-8, the level of IL-1β then did not decline, but remained elevated over the 24 h test period.

Figure 3A:
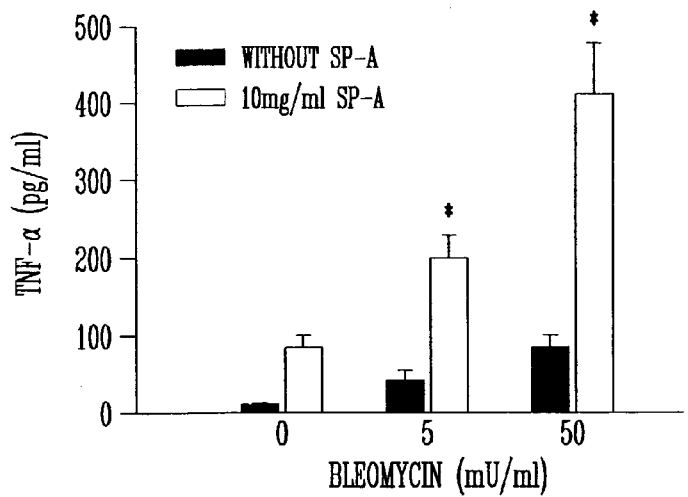
FIG. 3 illustrates the combined effect of SP-A and bleomycin on cytokine production by THP-1 cells. Differentiated THP-1 cells were stimulated with SP-A (10 µg/ml) and bleomycin (BLM 5, 50 mU/ml) simultaneously for 4 h or 6 h. TNF-α (Panel A) and IL-8 (Panel B) in culture medium at 4 h incubation and IL-1β (Panel C) at 6 h were quantified. Data are derived from 5 separate experiments, and the results are given as means±SEM. The indicated values (*) are significantly different (p<0.05) from points with SP-A alone and points with the same dose of bleomycin but without SP-A.
Figure 3B:
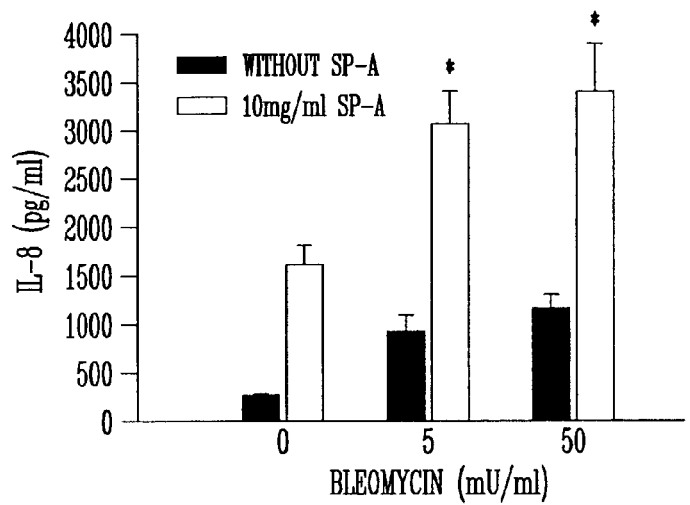
Figure 3C:
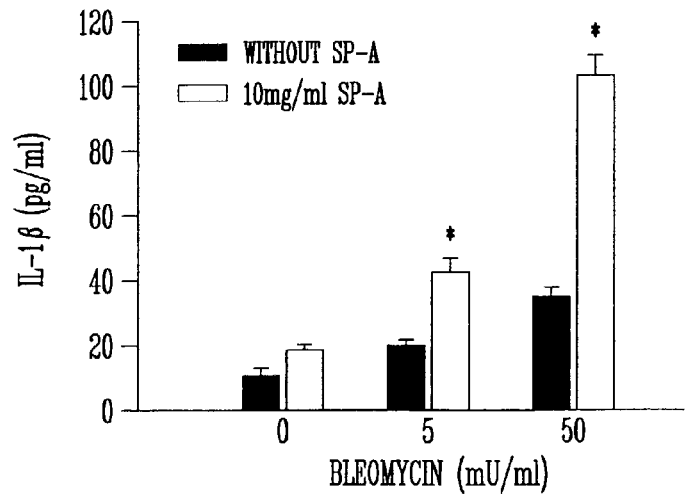

The Combined Effect of SP-A and Bleomycin on Cytokine Production and mRNA Expression by THP-1 Cells After testing the effects of bleomycin treatment on TNF-α, IL-1β, and IL-8 production by THP-1 cells, the combined effects of SP-A and bleomycin on cytokine production were examined. A dose of 10 μg/ml of SP-A was chosen rather than the dose of 50 μg/ml used in previous experiments, as the low dose may better identify synergistic or additive effects of the two substances. As shown in FIG. 3A, TNF-α values induced by SP-A (10 μg/ml) alone and bleomycin (5 mU/ml) alone were 86.6±11.5 pg/ml and 45.9±10.6 pg/ml, respectively. But the combined treatment increased the level to 201.7±34.3 pg/ml. High concentration of bleomycin (50 mU/ml) alone induced a TNF-α level of 82.1±17.3 pg/ml, while the value of the combined effect was 416±61.9 pg/ml. There was a similar response pattern for IL-8 when the combined effects of SP-A and bleomycin were examined (FIG. 3B). Because IL-1β reached a maximum value at a later time point than TNF-α and IL-8 did, we measured its level at 6 h after treatment. The means of IL-1β levels (FIG. 3C) induced by the combined treatment were greater than the sum of the separate means by SP-A or bleomycin alone as seen with TNF-α and IL-8. SP-A and bleomycin appear to have synergistic effects on TNF-α, IL-1β, and IL-8 production by THP-1 cells.

Figure 4A:
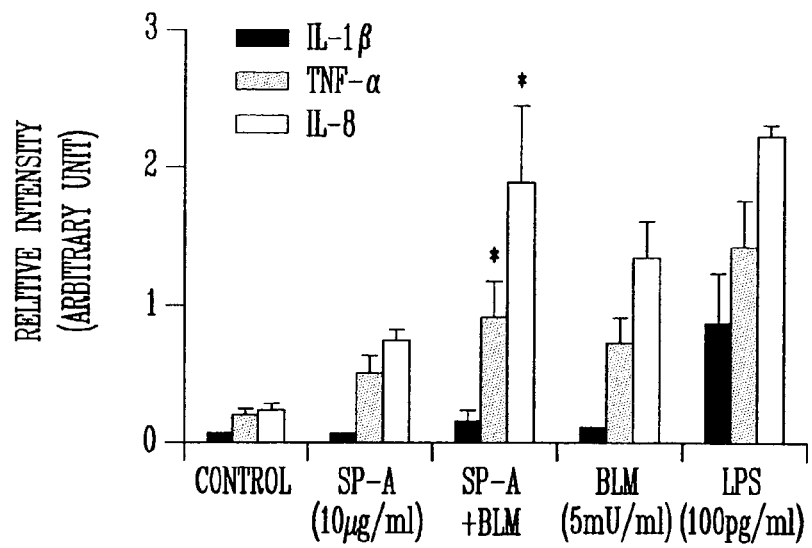
FIG. 4 illustrates the combined effect of bleomycin and SP-A on cytokine mRNA levels. Differentiated THP-1 cells were stimulated with SP-A (10 µg/ml) and/or bleomycin (BLM 5 mU/ml) simultaneously. After a 2 h (Panel A) or a 4 h (Panel B) incubation, the cells were processed for quantification of cytokine mRNA by RNAse protection assay (RPA). The mRNA level for TNF-α, IL-1β, and IL-8 in 2 µg of total cell RNA was normalized to mRNA for ribosomal protein L32. Data shown in Panel A and B were derived from 4 and 3 separate experiments, respectively. Results were given as means±SEM. The indicated values are significantly different (p<0.05) from points treated with SP-A (*) and bleomycin (^) alone, respectively. LPS (0.1 ng/ml) treatment was included as a positive control.
Figure 4B:
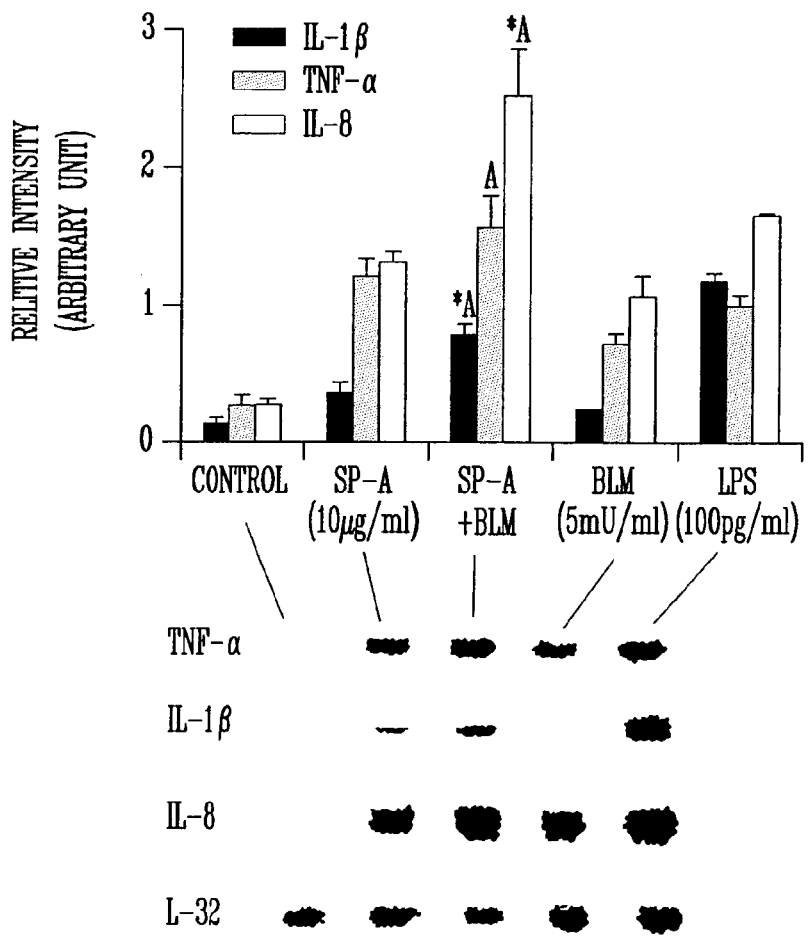

The mRNA levels of TNF-α, IL-1β, and IL-8 were measured by RPA. THP-1 cells were treated with SP-A (10 μg/ml) and/or bleomycin (5 mU/ml) for 2 h and 4 h separately. LPS-treated groups (0.1 ng/ml) were included as a positive control. After 2 h of incubation (FIG. 4A), TNF-α and IL-8 mRNA significantly increased as compared to the control ($p<0.05$). When the cells were treated with SP-A+bleomycin, the relative intensity of TNF-α mRNA increased from 0.51±0.27 (SP-A alone) to 0.95±0.21 ($p<0.05$), but no significant difference was observed between SP-A+bleomycin and bleomycin alone (0.95±0.21 vs. 0.74±0.20). A similar response pattern was also seen with IL-8 mRNA. Very low levels of IL-1β mRNA were detected in all SP-A- and bleomycin-treated cells, but LPS significantly increased the level of IL-1β mRNA at 2 h. The effect of SP-A and bleomycin on IL-1β mRNA expression at 4 h were greater than that at 2 h. A significant increase of IL-1β mRNA expression was observed when SP-A treatment was combined with bleomycin compared to bleomycin alone (FIG. 4B). The IL-8 mRNA level (2.47±0.75) following SP-A+bleomycin treatment was significantly higher ($p<0.05$) than that with SP-A alone (1.26±0.14) or bleomycin alone (1.02±0.16). For TNF-α the differences at 4 h did not reach statistical significance. These results together indicate an additive effect of SP-A and bleomycin on the TNF-α, IL-1β, and IL-8 mRNA expression.

Figure 5:
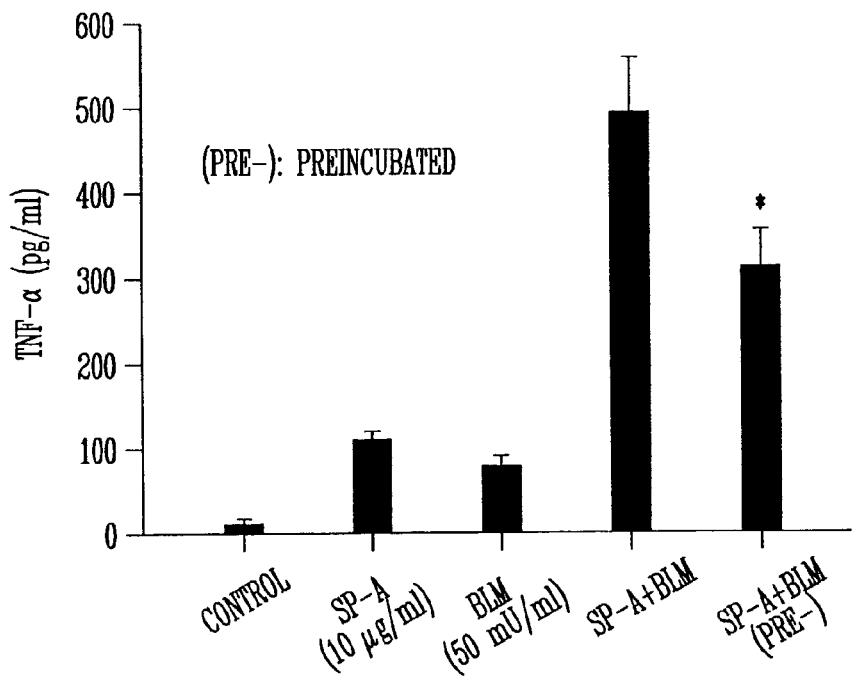
FIG. 5 illustrates the effect of preincubation of SP-A and bleomycin (BLM) on TNF-α production. Differentiated THP-1 cells were stimulated with SP-A (10 µg/ml) and bleomycin (50 mU/ml) that were either preincubated together for 15 min at 37° C. before adding them to the cells, or were not preincubated. Data are derived from 4 separate experiments. Results were given as means±SEM. The indicated values (*) are significantly different from points without preincubation.

When SP-A (10 µg/ml) was preincubated with bleomycin (50 mU/ml) 15 min before addition to the cells, the TNF-α level was significantly lower than that without preincubation (FIG. 5). However, the synergistic effects on TNF-α production remained. There was a similar response with respect to IL-8 production.

Figure 6:
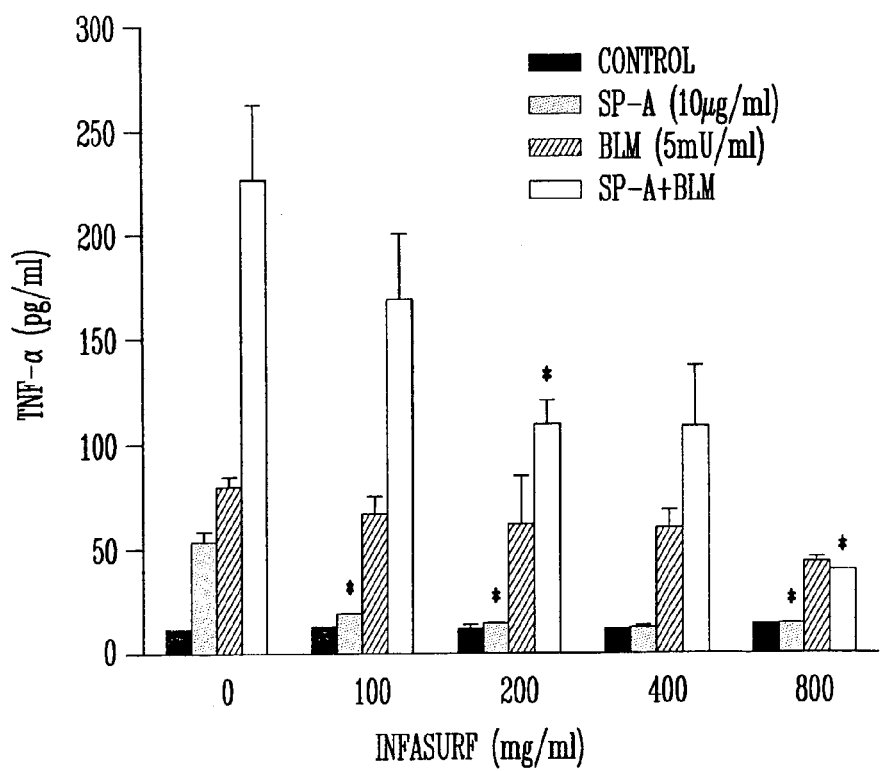
FIG. 6 illustrates the effect of surfactant lipids (Infasurf) on SP-A and bleomycin induced TNF-α production. Infasurf at indicated concentration was preincubated separately with SP-A (10 µg/ml), bleomycin (5 mU/ml), and SP-A+bleomycin for 15 min at 37° C. before addition to THP-1 cells. Incubation was continued for 4 h. Cells were incubated for 4 h after treatment. Culture medium was then collected and TNF-α level was quantified by ELISA. Data shown are from single experiment in triplicate, but are representative of three experiments. Results are given as means±SEM. The indicated values (*) are significantly different (p<0.05) from points obtained in the absence of Infasurf.

The Inhibitory Effect of Infasurf on SP-A and Bleomycin-Induced Cytokine Production and mRNA Expression The ability of surfactant lipids to modulate cytokine level was examined. As shown in FIG. 6, Infasurf had no effect on TNF-α level in the absence of SP-A and bleomycin. SP-A-induced TNF-α level was significantly reduced by Infasurf at 100 µg/ml and was totally inhibited with a higher dose of Infasurf. In contrast, the bleomycin effect was not significantly reduced by Infasurf even at 800 µg/ml. Infasurf decreased the TNF-α level induced by SP-A+bleomycin in a dose-dependent pattern. The TNF-α level was significantly decreased from 226.8±35.7 pg/ml in the absence of Infasurf to 109±19.3 pg/ml and 41.5±0.7 pg/ml at 200 µg/ml and 800 µg/ml of Infasurf, respectively.

Figure 7:
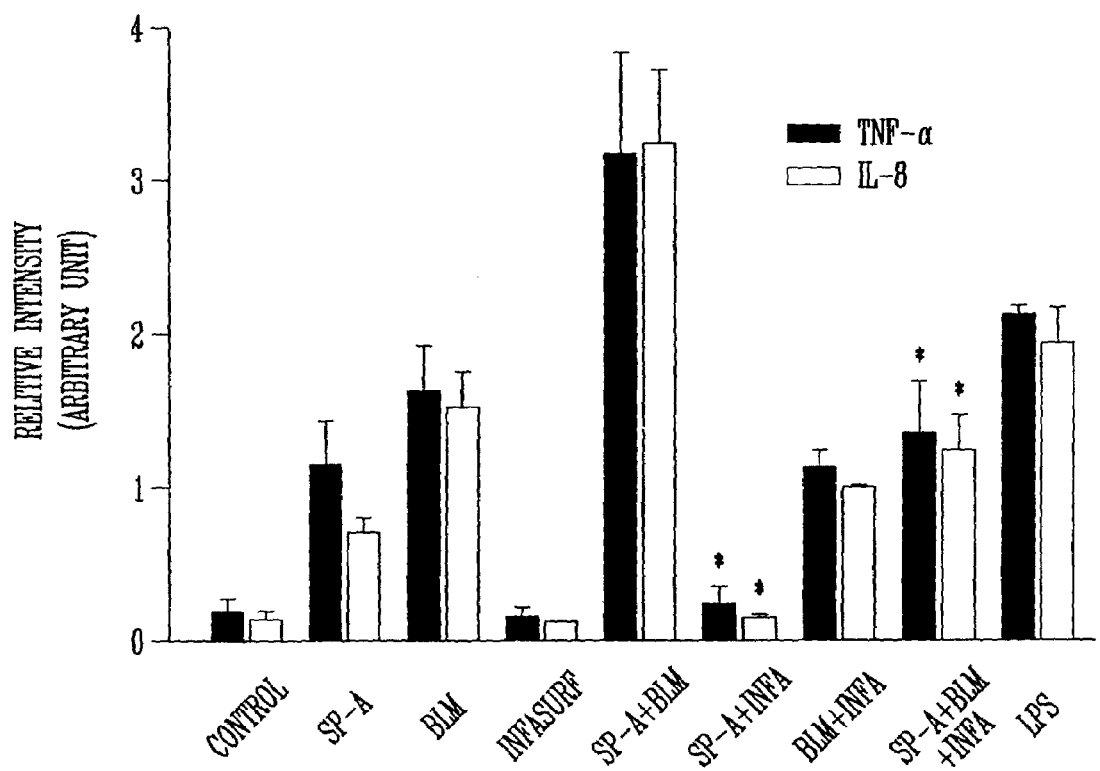
FIG. 7 illustrates the effect of surfactant lipids (Infasurf) on SP-A and bleomycin induced TNF-α, IL-8 mRNA expression. Infasurf (Infa; 400 g/ml) was preincubated separately with SP-A (10 µg/ml), bleomycin (5 mU/ml), and SP-A+bleomycin 15 min at 37° C. before addition to THP-1 cells. Cells were incubated for 4 h after treatment. Cells were processed for quantification of cytokine mRNA by RPA. The mRNA levels of TNF-α and IL-8 in 2 µg of total RNA was normalized to the mRNA of the housekeeping gene GAPDH. Data shown are from 3 experiments. Results are given as means±SEM. The indicated values (*) are significantly different (p<0.05) from points obtained in the absence of Infasurf. BLM: bleomycin.

Similar results were obtained when TNF-α and IL-8 mRNA expression was measured by RPA (FIG. 7). TNF-α mRNA expression induced by SP-A was totally inhibited by Infasurf (400 µg/ml), but at the same time bleomycin-induced TNF-α mRNA level was not significantly changed. In SP-A+ bleomycin treatment, the relative intensity of TNF-α mRNA was decreased from 3.17±0.71 in the absence of Infasurf to 1.14±0.10 in the presence of Infasurf. A similar response pattern was also seen for IL-8 mRNA after Infasurf treatment.

Discussion

The study demonstrates that SP-A plays a role in bleomycin-induced inflammation and that surfactant lipids modulate this process. With the macrophage like THP-1 cell line, ribonuclease protection assay and ELISA were used and the following was observed: bleomycin (as has been shown for SP-A) enhances proinflammatory cytokine production by THP-1 cells. The combined blemycin/SP-A on cytokine production is additive by ribonuclease protection assay and synergistic by ELISA. No effect on cytokine production is observed by Ara-C, a chemotherapeatic agent that has not been associated with lung inflammation and fibrosis, suggesting that the effect is specific to bleomycin and/or to agents or conditions associated with lung inflammation and fibrosis. The surfactant lipids significantly suppress the additive or synergistic effect on cytokine production observed in the presence of both SP-A and bleomycin. These data indicate that surfactant lipids may be useful in the suppression of inflammatory processes induced by SP-A and bleomycin or other inflammatory agents and drugs. This in turn should prevent lung fibrosis, a serious complication of chemotherapeutic agents such as bleomycin and other inflammatory agents.

Bleomycin stimulates THP-1 cells, a cell line of monocytic origin that upon vitamin $D_3$ differentiation acquires macrophage-like phenotype, to secrete cytokines in dose- and time-dependent patterns. The TNF-α time course observed is comparable to clinical observations about circulating TNF-α level after bleomycin treatment. Although some differences between the THP-1 cell line and alveolar macrophage were apparent in the kinetics and level of TNF-α and IL-1β indduced by bleomycin treatment, the data presented demonstrates the usefulness of the THP-1 cell line as a model system for the study of bleomycin-induced cytokine production. Ara-C, another chemotherapeutic agent, can also cause pulmonary complications, but this is typically non-cardiogenic pulmonary edema rather than inflammation and fibrosis.

It has now been shown that SP-A in low dose (10 µg/ml) significantly increased cytokines at both the protein and mRNA levels. LPS (0.1 ng/ml) was used as a positive control. A striking difference in IL-1β mRNA expression between LPS and SP-A treated cells was observed, especially at 2 h after treatment (FIG. 3A). The relative intensity of IL-1β mRNA induced by LPS was 18-fold greater than that induced by SP-A (0.92±23 vs 0.05±0.02), while the differences between LPS and SP-A in TNF-α or IL-1β mRNA are only around 2-fold. These data may indicate that the regulation of proinflammatory cytokine production by SP-A in THP-1 cells occurs by a different pathway than that utilized by LPS.

EXAMPLE 2

Evidence of SP-A in the Vaginal Mucosa

Materials and Methods

Collection of Vaginal Tissue and Fluid

Human vaginal tissue was obtained from 12 pre- and 12 poatmenopausal patients undergoing hysterectomy for benign uterine disease or vaginal repair for low-grade cystocele or rectocele. In nine of the premenopausal patients, hysterectomy specimens were available for histological dating of the endometrium to determine the stage of the menstrual cycle. Based on criteria of Noyes, Hertig and Rock (1), five of the nine premenopausal specimens were from women judged to be in the proliferative phase, two in the mid-cycle, and two in the secretory phase of the cycle. Of the 12 postmenopausal patients, two were prescribed oral conjugated equine estrogens and two topical conjugated equine estrogens. The other eight were not receiving any form of hormonal replacement. Full thickness fresh surgical specimens, that included epithelium and the underlying lamina propria, were fixed for 12 to 24 hours in 10% neutral-buffered formalin for immunocytochemistry (ICC) or snap frozen at −80° C. for extraction of RNA 49. Vaginal fluid was sampled from 10 healthy prem nopausal volunteer subjects during the follicular,ovulatory and luteal phase of the cycle over the course of 3 months. Ovulatory samples were collected within 18 hours after the detection of urine luteinizing hormone. Luteal phase samples were collected 7 to 9 days following ovulation, and follicular phase samples were collected on the first day after the resolution of menses. Vaginal fluid was collected by rinsing the vaginal wall repeatedly with 2 ml of normal saline, and stored at −80° C. until use. Tissues were collected according to protocols approved by the Institutional Review Board of the College of Medicine of the Pennsylvania State University.

Analysis of Vaginal Tissue SP-A Protein

Antibody: A rabbit polyclonal anti-human SP-A IgG, raised against SP-A from alveolar proteinosis material that was purified by isoelectric focusing, has been previously described (2).

Immunocytochemistry: Sections (4 µm) from formalin-fixed paraffin-embedded full-thickness vaginal epithelium with underlying lamina propria were processed using low temperature antigen-retrieval for ICC as described previous (3). The primary antibody was used at dilutions of 1:500 to 1:1000. The signal from the biotinylated goat anti-rabbit secondary antibody was amplified using Vectastain ABC reagent (Vector, Burlingame, Calif.) with alkaline phosphatase as the reporter and Vector Red™ (Vector, Burlingame, Calif.) or bromo-chloro-indolyl phosphate (BCIP) and nitroblue tetrazolium (NBT) (Sigma Chemical Co., St. Louis, Mo.) as the substrate and chromogen, respectively. Endogenous alkaline phosphatase was inhibited by preincubating sections with 0.2 N HCl for 5 min. From each tissue block two adjacent sections were processed for ICC. One of these was not counterstained while the other was exposed briefly with hematoxylin to stain nuclei. Control sections were incubated with pre-immune serum followed by secondary antibody, or with secondary antibody only. Sections were viewed by two of the authors (JW and CM) first independently and then together. Images were recorded with a Nikon DXM 1200 digital camera under Nomarski optics and using Nikon ACT1 version 2 software.

Analysis of Vaginal Tissue for SP-A mRNA

In order to confirm that SP-A is expressed in vaginal epithelium, total RNA isolated from vaginal mucosa was examined for the presence of transcripts of SP-A by Northern analysis. In addition, RT/PCR was carried out so as to determine if both of the two linked genes encoding SP-A in humans, SP-A1 and SP-A2, are expressed in the human vaginal mucosa. While SP-A transcribed from these two genes differ by fewer than ten amino acid residues, these differences have been shown to affect host-defense functions in vitro.

Preparation of RNA: Tissues (approximately 200 mg) stored at −80° C. were homogenized in 2 ml RNAzol B (Tel-Test, Friendswood, Tex.) using a glass-Teflon Dounce homogenizer. After adding an equal volume of chloroform, the homogenate was shaken vigorously for 15 seconds, chilled on ice for 5 min and centrifuged at 12,000×g at 4° C. for 15 min. The aqueous phase was collected and total RNA precipitated with an equal volume of isopropanol.

Northern analysis: Twenty μg total RNA from vaginal mucosa or lung (positive control) was separated on a 1% agarose-formaldehyde gel, transferred onto a GeneScreen Plus membrane (NEN, Boston, Mass.) and immobilized by UV cross-linking. The membrane was hybridized with a $^{32}$P-labeled antisense SP-A probe ($10^6$ cpm/ml) in ULTRAhyb solution (Ambion, Austin, Tex.) at 68° C. overnight, washed according to the manufacturer's instructions and exposed to Kodak XAR 5 film at −80° C.

RT-PCR and sequencing: Total RNA (100 ng) was incubated with 15 ng of oligo-dT primer at 70° C. for 10 min and then cooled to room temperature for 15 min. Reverse transcription was carried out using Maloney murine leukemia virus reverse transcriptase (Gibco BRL, Gaithersburg, Md.), as described previously (6). One μl of the reaction product was used as a template in a 50 μl PCR. The primers, 5'gacgtttgtgttggaagccctgg3' (sense)(SEQ. ID. NO:1) and 5'ggtaccagttggtgtagttcacag3' (antisense)(SEQ ID. NO:2), amplify a 578 bp segment spanning SP-A1 and SP-A2 exons one through four. This segment includes sequences that differentiate between transcripts from SP-A1 and SP-A2, the two linked genes that encode SP-A. The PCR buffer, primer, dNTP and Taq polymerase concentrations used were those recommended by the manufacturer (Applied Biosystems, Inc., Foster City, Calif.). Cycle parameters were as follows: 94° C. denature for 2 min, then 94° C. denature for 45 seconds, 58° C. anneal for 45 seconds, 72° C. extension for 45 seconds for 35 cycles. Reaction products were separated by a 2% agarose gel containing ethidium bromide. Gel bands (approx 578 bp) from two subjects (approx 578 bp) were excised, the DNA extracted and cloned into a PCR11 plasmid (Invitrogen, Carlsbad, Calif.). Eight clones from each of two subjects were sequenced in both directions by the Penn State College of Medicine Biomolecular Core Facility.

Analysis of Vaginal Lavage Fluid for SP-A Protein

To determine whether SP-A was secreted into the vaginal fluid phase, lavage fluid was analyzed for SP-A by gel-electrophoresis and the sequence of SP-A immunoreactive protein isolated from such gels was determined by mass spectrometry.

Two-dimensional (2-D) gel electrophoresis and immunoblotting: To disrupt aggregates present in the vaginal fluid, Tris-HCl was added to the vaginal lavage to a final concentration of 1 mM, EDTA to 1 mM and Tween 20 to 0.1%. Resulting solutions were cleared of cellular debris by centrifugation at 150×g for 1 min. The supernatant was concentrated 20-fold using an Ultrafree-MC (10,000 m.w. cut off) microconcentrator (Millipore Corp., Bedford, Mass.) and resuspended in a mixture of 2-D lysis buffer and sample buffer (3:1, Amersham Biosciences, Piscataway, N.J.). Isoelectric focusing was performed in duplicate by loading a 50 μl aliquot on each 11 cm gel strip containing an immobilized pH 3–10 gradient (Immobiline DryStrip, Amersham Biosciences, Piscataway, N.J.) and run for 9 h at 300 V, then 8 h at 2990 V (30870 V/hours). Proteins were separated in the second dimension on a horizontal 12.5% SDS-polyacrylamide ExcelGel (Amersham Biosciences, Piscataway, N.J.). One of two gels was transferred to a nitrocellulose membrane (Trans-Blot, 0.45 μm, Bio-Rad Laboratories Inc., Hercules, Calif.) using a NovaBlot transfer apparatus (Amersham Biosciences, Piscataway, N.J.). The membrane was blocked with 1% BSA in PBS and immunostained using anti-human SP-A primary antibody, followed by HRP-conjugated goat anti-rabbit secondary antibody. The signal was detected with Western Lightning enhanced chemiluminescence reagent (Perkin Elmer Life Sciences, Boston, Mass.). The other gel was silver-stained, using a glutaraldehyde-free method of sensitization, according to the manufacturer's instructions (SilverQuest, Invitrogen Corp., Carlsbad, Calif.). The gel was then washed in water for 10 min, drained and photographed with a Polaroid camera. The silver-stained gel was overlaid on the radiograph of the immunostained gel, and silver-stained gel spots corresponding to anti-SP-A immunoreactive spots were excised for mass spectrometry. A comparable size piece of gel from a protein-free area of the gel was excised as a negative control for mass spectrometry.

Mass spectrometry: In order to determine the nature of the immunoreactive protein identified by 2-D gel immunoblot, tryptic peptides from gel fragments were analyzed by matrix-assisted laser desorption ionization—time of flight mass spectrometry (MALDI-TOF MS). Excised silver-stained gel fragments were destained and were subject to partial trypsin digestion by dehydrating the gel fragments in 100% methanol for 5 min, rehydration in 30% methanol in water, followed by 3 washes for 10 minutes each in 100 mM ammonium bicarbonate, 30% acetonitrile. The gel pieces were crushed, rinsed in water and dried in a Speed Vac for 30 min. Gel pieces were resuspended in 50 mM ammonium bicarbonate buffer containing sequencing grade trypsin (Promega Corp., Madison, Wis.) 7 ng/l buffer, and incubated overnight at 37° C. The supernatant was collected following high-speed centrifugation for 1 min. Remaining peptides were extracted from the gel pieces with 20 μl 50% acetonitrile and 0.1% trifluoroacetic acid and then combined with the above supernatant. Solutions were concentrated to 5 μl in a Speed Vac and submitted to the Penn State College of Medicine Core Facility for mass spectrometry.

Tryptic peptides were mixed with an equal volume of matrix (α-cyano-4-hydroxy trans cinnamic acid), passed through a Zip-Tip and spotted onto a stainless steel sample stage where the sample was allowed to evaporate at room temperature. Mass spectra were obtained with a Reflectron MALDI-TOF mass spectrophotometer (Voyager DE-PRO, PerSeptive Biosystems/Applied Biosystems, Foster City, Calif.). Peptide spectra were calibrated using several matrix ion peaks as internal standards and compared to that of human SP-A amino acid sequence (gi:13346506) from the NCBI database.

Concentration of SP-A and cytokines in vaginal fluid during the menstrual cycle: The concentration of SP-A, IL-1β and IL-8 in vaginal lavage fluid was measured in the follicular, ovulatory and luteal phase of the menstrual cycle. The phase of the cycle was determined as described above. Indirect ELISA, previously described, was used to measure SP-A, with the exception that vaginal fluid was diluted 332:1 in coating buffer. Vaginal lavage IL-1β and IL-8 concentrations were measured by ELISA according to the manufacturer's instructions (OptEIA, BD Biosciences, Chicago, Ill.). Vaginal fluid was diluted 20:1 in sample diluent for IL-1β and IL-8 ELISA.

Statistical analysis: Differences in the concentration of SP-A and cytokine in vaginal lavage fluid were tested for significance with a repeated measures analysis of variance test using the Bonferroni correction.

Results

Localization of SP-A in the Vaginal Mucosa

In all sections from premenopausal donors, SP-A immunoreactive protein was present in the vaginal epithelium and localized in two distinct regions, in the cytoplasm of cells in the deep portion of the intermediate layer that is adjacent to the parabasal layer, and in the superficial layer. The deep intermediate layer contains cells that are accumulating glycogen and beginning the process of progressive loss of biosynthetic organelles as they undergo terminal differentiation, whereas the superficial layer contains essentially dead cells with pyknotic nuclei that are destined to be shed into the vaginal lumen. There were no obvious differences in localization or intensity of the immunoreactive protein as a function of the ovarian cycle, as determined by histological dating of endometrium obtained at the time of hysterectomy. There was no immunostaining seen in cells in the upper intermediate layer, the layer that separates the strongly immunopositive deep intermediate and superficial layers. This is in contrast to glycogen which is present throughout the intermediate layer. Pre-treating sections with α-amylase did not affect immunostaining for SP-A indicating that glycogen did not affect SP-A immunostaining. Cells in the basal layer, where epithelial stem cells are localized, and cells in the parabasal layer that separates the basal from the intermediate layer, were consistently immunonegative.

Immunostaining within the superficial layer in some specimens appeared continuous, while in others it was interrupted by weakly or minimally immunopositive regions. It should be noted, however, that since this study was carried out on surgical specimens, part of the superficial layer was in all probability removed during preparation of the vaginal mucosa for surgery. In one study, wiping the vaginal mucosa with rough absorbent paper was reported to decrease glycogen concentration of vaginal epithelium by about 20%.

Control sections pre-incubated with pre-immune serum or with secondary antibody only were uniformly negative.

As expected, in specimens from post-menopausal women there were marked differences in the thickness of the mucosa, the intermediate layer was narrowed, and stratification was less evident. Nevertheless, SPA-immunostaining was present in all of the specimens and was localized, as in the pre-menopausal epithelium, in cells adjacent to the parabasal layer and in the superficial layer. The distribution of such immunopositive cells in the vaginal epithelium from post-menopausal subjects, like the structural organization the epithelium, varied greatly. Groups of cells with strong immunostaining could be seen interposed between cells with minimal immunostaining. In four of the 12 specimens from postmenopausal subjects the epithelium was markedly thickened (acanthosis) and appeared to be covered by an immunonegative keratinized layer. These changes are likely to be due to trauma associated with prolapse of the vaginal vault, the reason for surgical repair of the vagina. Changes suggesting estrogenization of the vagina were seen in only one of the patients prescribed equine estrogen. There was no information as to whether the other three patients were taking the estrogens as prescribed. Together, these findings suggest that SP-A is expressed in the vaginal epithelium constitutively, and is not dependent on ovarian hormones.

Identification of SP-A Transcripts in the Vaginal Mucosa.

To determine the presence and size of SP-A transcripts in the vagina, total RNA isolated from the vaginal mucosa was subjected to Northern analysis, with RNA from lung serving as positive control. SP-A transcripts were identified from RNA from the vagina were found to be equal in length to those from the lung. However, while the signal from hybridization to the transcripts from lung could be obtained after 10 min exposure of the membrane, obtaining a comparable signal from vaginal RNA required a 36 h exposure. In interpreting this difference in relative abundance of SP-A transcripts in the two tissues it is important to keep in mind differences between them in the proportion of cells expressing SP-A. In lung, approximately 16% of the tissue used for RNA extraction is comprised of cells that express SP-A, the type II pneumocytes. According to the immunocytochemical findings, SP-A expression is essentially limited to cells in the deep intermediate layer of the vaginal epithelium. These clearly constitute only small fraction of the cells present in the full thickness tissue specimens (epithelium+lamina propria) from which the RNA was extracted. The superficial layer that also shows intense immunostaining is comprised mostly of dead cells that are an unlikely source of transcripts.

Vaginal RT-PCR products from three individuals were obtained. The size of the amplicon from each of the vaginal samples was identical to that from the lung. To determine whether SP-A transcripts in the vagina are derived from one or both SP-A genes, clonally selected RT-PCR products from two of the tissue donors were sequenced. Sequence comparison indicates that the vaginal transcripts are identical to those characterized in the lung, and that both SP-A1 and SP-A2 transcripts are expressed. Although the SP-A cDNA from the vagina that was sequenced is not full length, the Northern analysis indicates that lung and vaginal transcripts are identical in size. Therefore, portions of the vaginal SP-A cDNA that were not analyzed at the sequence level, including the 5' UTR and 3' UTR regions, would not be expected to be significantly different from those previously characterized from the lung. It will require determining the full sequence including 3' and 5'UTR regions to exclude the possibility of small tissue-specific differences that may affect gene expression.

SP-A is Present in the Vaginal Fluid Phase

The presence of SP-A immunoreactive cells in the superficial layer of the vaginal mucosa led us to postulate that SP-A may be released into the fluid phase associated with the vaginal mucosal surface. Indeed, immunoreactive SP-A was identified in fluid collected by lavage from a healthy pre-menopausal donor and separated by 2-D SDS-PAGE. A comparison of the 2-D gels of human lung SP-A and vaginal fluid SP-A revealed that the latter has an isoelectric point that is slightly more basic and that it has an apparent molecular mass of 60–70 kDa, slightly higher than that of the SP-A dimer from the lung.

To confirm the identity of the protein detected in the vaginal lavage, mass spectrometry (MALDI-TOF) was used to analyze tryptic peptides from the silver-stained gel spot that corresponded to the SP-A immunoreactive spot. The peptides were found to cover 55% of the amino acid sequence of pulmonary SP-A. This greatly exceeds the 15% coverage that is considered sufficient to establish the identity of a protein.

The Concentration of SP-A and Proinflammatory Cytokines in Vaginal Lavage Fluid are Increased in the Follicular Phase In order to test the postulate that SP-A concentration in vaginal fluid is related temporally to cyclic changes in proinflammatory cytokines, vaginal lavage fluid SP-A and cytokine concentrations were measured at 3 distinct times of the menstrual cycle. These healthy volunteers were devoid of subjective and objective evidence of vaginitis. Concentration of SP-A in vaginal fluid in the follicular phase was significantly increased above that found in the ovulatory ($p<0.018$) and luteal ($p<0.009$) phase of the cycle. There was no significant difference in SP-A concentration between ovulatory and luteal concentrations ($p<0.227$). Notably, the concentration of both IL-1$\beta$ and IL-8 were significantly increased in the follicular phase compared with ovulatory levels ($p<0.018$, IL-1$\beta$)($p<0.10$, IL-8). There was no significant difference in the concentration of two cytokines between ovulatory and luteal ($p<0.939$, IL-1$\beta$; $p<0.491$, IL-8) concentrations.

Together, the findings provide evidence for the presence of immunoreactive SP-A in the vaginal epithelium at two discrete sites, of SP-A protein in the vaginal fluid phase, and that both SP-A1 and SP-A2 genes are expressed in the vaginal epithelium.

Discussion

Locally produced factors that modulate host response to pathogens represent an early and critical aspect of host-defense. The data presented here indicate that one such factor, SP-A, is produced in the vaginal epithelium within a specific epithelial cell population in the intermediate layer, is concentrated in the superficial layer and can be recovered intact from the vaginal lavage fluid. The finding of lack of any obvious cyclic changes in SP-A immunoreactivity in the pre-menopausal vaginal epithelium, and, more importantly, its persistence in the post-menopausal vaginal epithelium, indicate that SP-A is expressed in this tissue constitutively, independent of ovarian hormones.

The discrete localization of SP-A immunoreactivity in the deep intermediate layer, adjacent to the basal layer of the vaginal mucosa, is consistent with the notion of its participation in the afferent arm of the immune response in this tissue. According to the current understanding of early responses of the vagina to pathogens, phagocytic cells in the dermis and the basal and parabasal layers of the squamous epithelium traverse intercellular channels permeating the epithelium, sample pathogens, then return to local subdermal lymphoid aggregates where antigen presentation occurs. Langerhans cells, the resident dendritic cells in the vagina, and one of the putative targets of SP-A, have also been identified in the deep intermediate layer. The localization of cells expressing SP-A in the same layer puts this collectin in place to contribute to the process of antigen presentation and activation of dendritic cells. Similarly, the concentration of SP-A in the superficial layer of the vaginal mucosa clearly places it at a strategic site for participating in the immediate, innate immune component of host-defenses. However, the fact that the immunopositive superficial layer is separated from those producing it in the deep intermediate layer by several strata of immunonegative cells raises two questions. How does SP-A reach the superficial layer and what is responsible for anchoring SP-A to this layer?

A plausible answer to the first question is provided by evidence for the presence of channels between cells throughout the intermediate layers. These channels are a likely route for transfer of SP-A from cells in the deep intermediate to the surface layer of the vaginal mucosa. If so, SP-A would be expected to have an extra-cellular localization in the superficial layer. Therefore, to address the question of what is responsible for the concentration of SP-A in the superficial layer requires considering the composition of the material occupying the extracellular space. The presence of a significant extracellular space, occupied by material that stains with basic fuchsin Schiff reagent and is resistant to $\alpha$-amylase, and that surrounding cells of the superficial layer of the vaginal epithelium was first described over half a decade ago. The staining has been attributed to polysaccharides and/or glycoproteins and constitutes an example of a prominent glycocalyx. While the composition of the glycocalyx in the superficial layer of the human vagina remains to be determined, it is reasonable to propose that it would include molecules with domains with which SP-A could associate via its carbohydrate recognition domain. Together, the findings direct attention to the need to consider the importance of extracellular components of the vaginal epithelium in host-defense.

The demonstration of an increase in the concentration of SP-A in the vaginal fluid in the follicular phase of the cycle also places SP-A in a position to take part in the regulation of inflammatory responses. This concept is supported by the inventors' finding of a corresponding increase in vaginal fluid proinflammatory cytokines that parallels previously reported cyclic increases in local, but not circulating, cytokine concentrations and leukocytes. This demonstrates that SP-A contributes to the local modulation of inflammation.

The demonstration that both SP-A1 and SP-A2 genes are expressed in the vaginal mucosa has functional implications. In the lung two gene products have been described. Functional differences between SP-A derived from a single gene and SP-A derived from both genes have been reported. For example, cytokine production by macrophage-like THP-1 cells is greater when cells are treated with in vitro expressed SP-A2 than with SP-A1, and is greater upon treatment with co-expressed SP-A1 and SP-A2 than with either SP-A1 of SP-A2 alone.

Finally, it should be noted that the electrophoretic characteristics of vaginal SP-A differ somewhat from those of lung. These characteristics in lung SP-A are, in large part, due to various post-translational modifications, including glycosylation, sialylation, acetylation and proline hydroxylation, modifications that may affect function.

In conclusion, SP-A is expressed in the vaginal mucosa, is localized in specific cellular layers and can be recovered from the fluid phase. Together, the findings support the conclusion that SP-A has a functional role in host-defense in the vagina. Knowledge of the basis for qualitative and quantitative alterations of vaginal SP-A has the potential to contribute to our understanding of the pathogenesis of both local and ascending inflammatory conditions of the female genital tract. These include conditions that have substantial impact on human health, notably, STDs and preterm labor.

Having described the invention with reference to particular compositions, theories of effectiveness, and the like, it will be apparent to those of skill in the art that it is not intended that the invention be limited by such illustrative embodiments or mechanisms, and that modifications can be made without departing from the scope or spirit of the invention, as defined by the appended claims. It is intended that all such obvious modifications and variations be included within the scope of the present invention as defined in the appended claims. The claims are meant to cover the claimed components and steps in any sequence, which is effective to meet the objectives there intended, unless the context specifically indicates to the contrary.

For the above-stated reasons, it is submitted that the present invention accomplishes at least all of its stated objectives.

---

---

What is claimed is:

1. A method of reducing SP-A induced vaginitis comprising: administering to a female animal a small but effective amount of a composition comprising surfactant lipids.

2. The method of claim 1 whereby the surfactant lipids are administered in one or more doses of about 1–5 mg per dose.

3. The method of claim 1 wherein the surfactant lipids are administered once daily.

4. The method of claim 1 wherein the surfactant lipids are administered in divided doses.

5. The method of claim 1 wherein the surfactant lipids are administered as part of a treatment regimen that includes administration of at least one other agent used to treat vaginitis.

6. The method of claim 5 wherein the other agent is an antibiotic or an antifungal agent.

7. The method of claim 6 wherein the antibiotic is selected from one or more of the group consisting of clindamycin, ampicillin, metronidazole, tetracycline, and ceftriaxone.

8. The method of claim 6 wherein the antifungal is selected from one or more of the group consisting of miconazole, clotrimazole, econazole, butoconazole, tioconazole, and terconazole.

9. The method of claim 1 wherein the surfactant lipids are administered upon detection of symptoms of vaginitis.

10. The method of claim 1 wherein the composition further includes a pharmaceutically acceptable carrier.

11. The method of claim 1 wherein the composition is administered by a method selected from the group consisting of intratracheally, orally, subcutaneously, intravenously, intranasally, rectally, sublingually, intravaginally, and buccally.

12. The method of claim 11 wherein the composition is administered intravaginally.

* * * * *

UNITED STATES PATENT AND TRADEMARK OFFICE
CERTIFICATE OF CORRECTION

PATENT NO. : 7,041,638 B2
APPLICATION NO. : 10/428598
DATED : May 9, 2006
INVENTOR(S) : Joanna Floros et al.

It is certified that error appears in the above-identified patent and that said Letters Patent is hereby corrected as shown below:

Col 1, Line 13:

DELETE:
After invention "was funded in part by grants NIH R21 DE-14041, PHS PO1 AI-37829, NIH R21 DE-14041, and NIH 5R37HL-034788-16."

ADD:
After invention --was made with government support under Grant Nos. R01 ES09882, R37 HL34788, R21 DE14041 and P01 AI37829 awarded by the National Institutes of Health.--

DELETE:
After Government "may have"

ADD:
After Government --has--

Signed and Sealed this

Twenty-second Day of June, 2010

David J. Kappos
*Director of the United States Patent and Trademark Office*